United States Patent
Denison et al.

(10) Patent No.: US 6,575,996 B1
(45) Date of Patent: Jun. 10, 2003

(54) FILTER DEVICE FOR EMBOLIC PROTECTION SYSTEM

(75) Inventors: Andy Denison, Temecula, CA (US); Benjamin C. Huter, Murrieta, CA (US); Scott J. Huter, Temecula, CA (US); John D. Whitfield, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/895,784

(22) Filed: Jun. 29, 2001

(51) Int. Cl.$^7$ .............................................. A61M 29/00
(52) U.S. Cl. ..................................................... 606/200
(58) Field of Search ................................ 606/200, 159, 606/191, 195, 198, 194, 180; 604/22, 104, 96, 101; 128/898, 899

(56) References Cited

U.S. PATENT DOCUMENTS

| | | | |
|---|---|---|---|
| 4,723,549 A | 2/1988 | Wholey et al. | |
| 4,997,435 A | 3/1991 | Demeter | |
| 5,100,425 A | 3/1992 | Fischell et al. | |
| 5,158,548 A | 10/1992 | Lau et al. | |
| 5,375,612 A | * 12/1994 | Cottenceau et al. | 128/899 |
| 5,383,887 A | * 1/1995 | Nadal | 606/200 |
| 5,437,632 A | 8/1995 | Engleson | |
| 5,634,942 A | * 6/1997 | Chevillon et al. | 623/1 |
| 5,814,064 A | 9/1998 | Daniel et al. | |
| 5,827,324 A | 10/1998 | Cassell et al. | |
| 5,846,251 A | 12/1998 | Hart | |
| 5,911,734 A | 6/1999 | Tsugita et al. | |
| 5,968,071 A | 10/1999 | Chevillon et al. | |
| 5,980,555 A | 11/1999 | Barbut et al. | |
| 5,989,281 A | 11/1999 | Barbut et al. | |
| 6,171,327 B1 | * 1/2001 | Daniel et al. | 606/200 |
| 6,277,138 B1 | * 8/2001 | Levinson et al. | 606/200 |
| 6,346,116 B1 | 2/2002 | Brooks et al. | |
| 6,371,971 B1 | * 4/2002 | Tsugita et al. | 606/200 |
| 6,383,206 B1 | * 5/2002 | Gillick et al. | 606/200 |
| 6,394,978 B1 | * 5/2002 | Boyle et al. | 604/103.06 |

FOREIGN PATENT DOCUMENTS

| | | |
|---|---|---|
| WO | WO 01/10346 | 2/2001 |
| WO | WO 01/45592 | 6/2001 |
| WO | WO 01/87183 | 11/2002 |

\* cited by examiner

*Primary Examiner*—Gloria M. Hale
*Assistant Examiner*—Alissa L. Hoey
(74) *Attorney, Agent, or Firm*—Fulwider Patton Lee & Utecht, LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in a version of an embodiment thereof, enables the device to expand upon deployment thereof so as to seal off the inner surface of a blood vessel, to inhibit the forming of a gap therein, for inhibiting embolic material from passing therethrough. The system, in another version of the embodiment thereof, enables the device to navigate through confined spaces in tortuous anatomy.

28 Claims, 4 Drawing Sheets

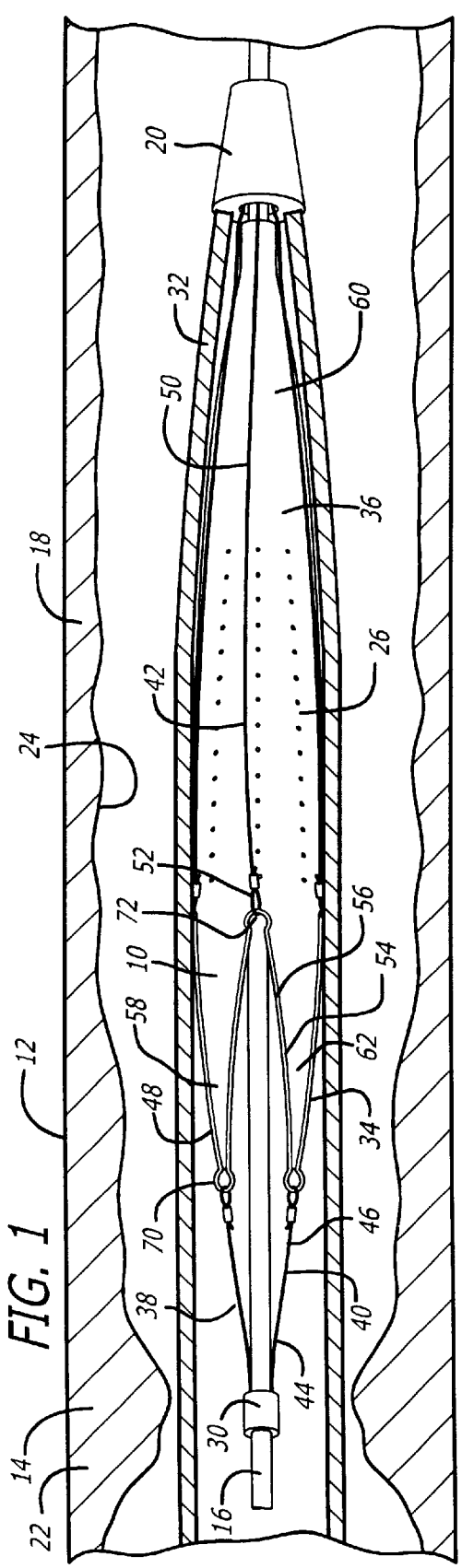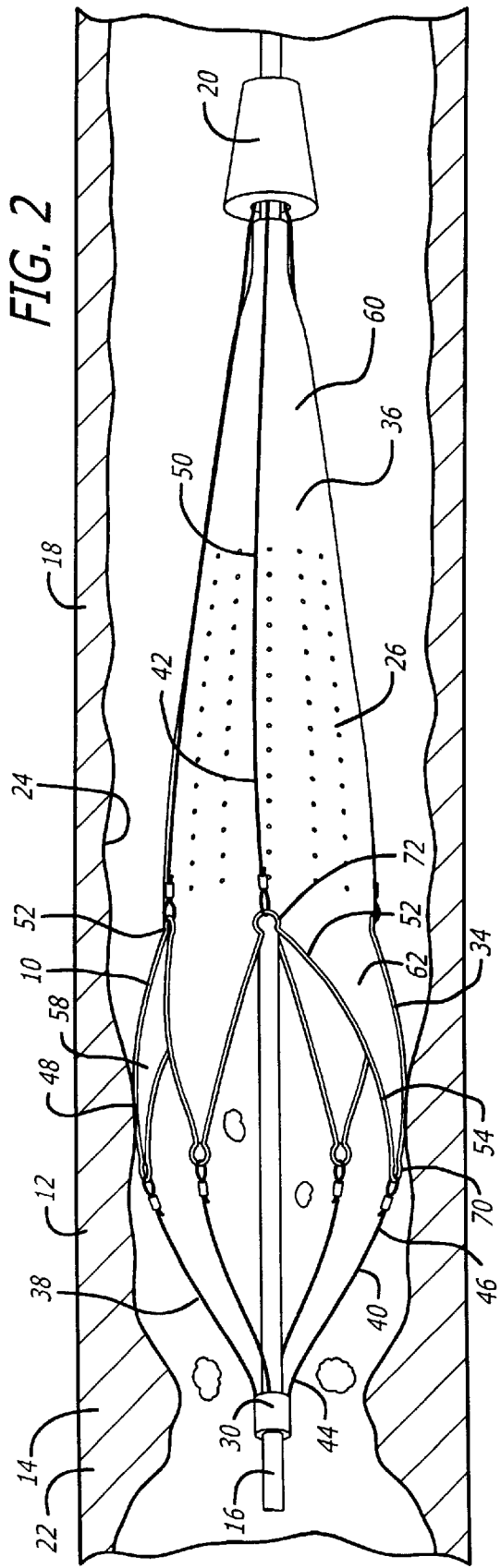

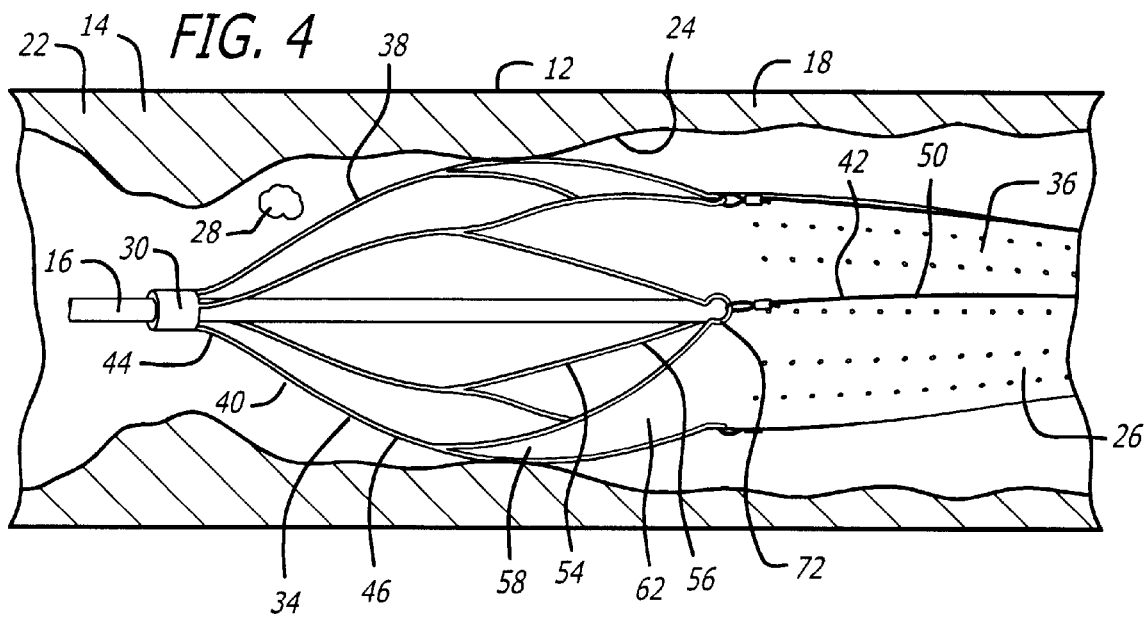
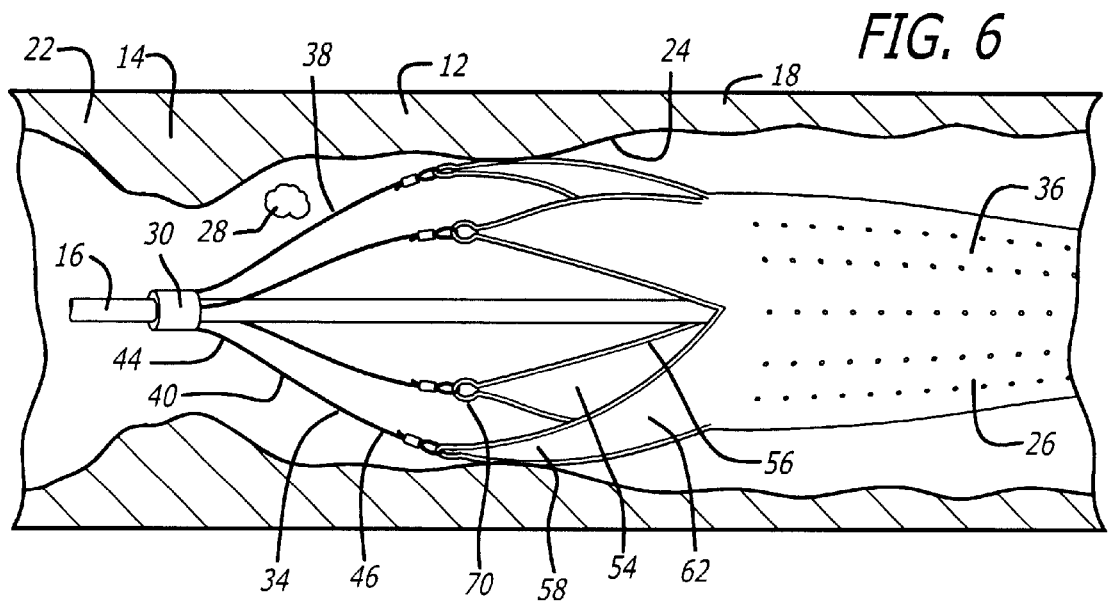

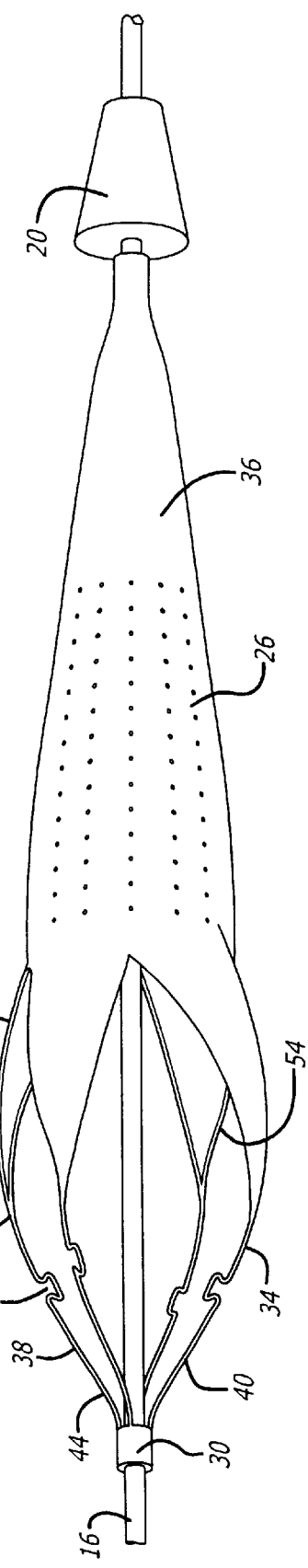

FILTER DEVICE FOR EMBOLIC PROTECTION SYSTEM

BACKGROUND OF THE INVENTION

The present invention relates generally to improvements in embolic protection systems and methods. In particular, it relates to an improved system and method for enabling an embolic protection device to be effectively inserted through a patient's vasculature and through confined spaces therein, to a location in a blood vessel distal to an interventional procedure site. The embolic protection device is also efficiently and conveniently deployed at the location distal to the interventional procedure site, to effectively expand against the inner surface of a blood vessel wall, so as to seal off the inner surface thereof. Such deployment enables the efficient capture embolic material which may be created and released into the bloodstream during the performance of the interventional procedure in a stenosed or occluded region of a blood vessel, and prevents embolic material from bypassing the embolic protection device.

The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel.

The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices are adapted to enable the filtering of embolic debris which may be released into the bloodstream during the treatment to the vessel, and yet allow a sufficient amount of oxygenated blood to flow past the device to supply vital organs downstream from the treatment site.

However, there have been problems associated with embolic protection devices, particularly during the insertion, and deployment thereof. The insertion of the device through the patient's anatomy in unexpanded condition within a delivery sheath to the position distal to the interventional procedure site may result in difficulty in negotiating the curvature of the patient's anatomy resulting from limited flexibility thereof. Also, the expansion and deployment of the embolic protection device may not result in full and complete expansion thereof, and consequently may not seal off the inner wall of the blood vessel about the entire circumference thereof, which can result in embolic material bypassing the device.

Therefore, the present invention provides improved systems and methods for treating stenosis in blood vessels which enable an embolic protection device to be efficiently inserted through a patient's vasculature to effectively navigate through confined spaces to a location distal to an interventional procedure site, and to expand so as to effectively seal off the inner surface of the blood vessel wall, to capture embolic material, and to prevent embolic material from bypassing the embolic protection device. Moreover, the systems and methods are relatively easy for a physician to use, while enabling the effective delivery and recovery of a filtering system capable of removing embolic debris released into the bloodstream. The inventions disclosed herein satisfy these and other needs.

SUMMARY OF THE INVENTION

The present invention, in general, provides a system and method for the insertion and removal of a filtering system for capturing and retaining embolic debris from a blood vessel. The embolic debris may be created during the performance of a therapeutic interventional procedure, such as a balloon angioplasty or stenting procedure. The filtering system prevents the embolic debris from lodging and blocking blood vessels downstream from the interventional site. The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient operation of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in a version of an embodiment of the present invention, a system is provided for enabling a filter deice to effectively expand against the inner surface of a wall of a blood vessel, and to seal off the inner surface thereof, for enabling the capture of embolic material which may be released into the blood vessel during the therapeutic interventional procedure.

The system includes a guide wire, including a distal end, which is positionable within the blood vessel so as to extend to a position distal to an interventional procedure site. The system also includes a filter device, which articulates so as to efficiently expand against the inner surface of the wall of the blood vessel, and to seal off the inner surface of a wall of the blood vessel, upon expansion for deployment thereof. Such expansion inhibits the formation of a gap between the filter device and the blood vessel wall, through which embolic material may otherwise flow.

In another version of the embodiment of the present invention, a system is provided which enables the insertion thereof through the patient's blood vessel to the position distal to the interventional procedure site, so as to efficiently navigate through confined spaces therein. The system includes a filter device which articulates so as to flex and move for navigating confined spaces in tortuous anatomy.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 1 is an elevational fragmentary partly-sectional view of a first form of a first version of the embodiment of the present invention, disposed within the internal carotid artery of a patient, including a delivery sheath and an unexpanded filter device.

FIG. 2 is a similar view of the first form of the first version of the embodiment shown in FIG. 1, wherein the delivery sheath has been removed and the filter device has expanded.

FIG. 4 is an elevational fragmentary partly-sectional view of a form of a second form of the first version of the embodiment of the present invention, disposed within the internal carotid artery of a patient, including an expanded filter device.

FIG. 6 is a view of a third form of the first version of the embodiment similar the view shown in FIG. 4.

FIG. 8 is an elevational view of a form of a second version of an embodiment of the present invention.

FIG. 9 is a similar view of another form of the second version of the embodiment shown in FIG. 8.

DETAILED DESCRIPTION OF THE PREFERRED EMBODIMENTS

Figure 3:
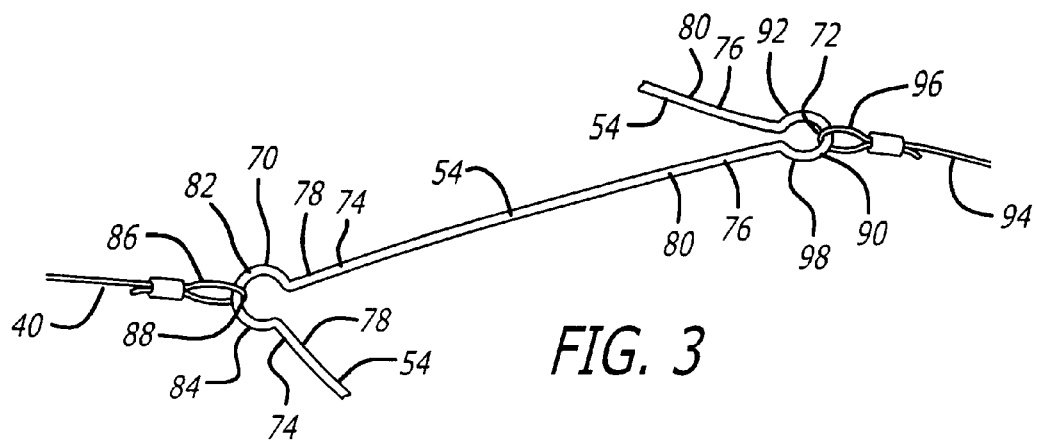
FIG. 3 is a fragmentary view of a portion of the articulating element in the filter device shown in FIGS. 1–2.

The present invention is directed to an improved system and method for enabling the capture of embolic material which may be released into the blood vessel during the therapeutic interventional procedure, in an efficient and effective manner. The invention enables a filter device to be inserted through a patient's anatomy so as to articulate therein, for enabling the filter device to navigate through confined spaces therein. It is further directed to such a filter device which articulates upon deployment thereof so as to expand against and seal off the inner surface of the blood vessel wall, to inhibit the formation of a gap through which embolic material may otherwise flow.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous vein grafts and other peripheral arteries. Additionally, the present invention can be utilized when performing any one of a number of interventional procedures, such as stenting, balloon angioplasty, laser angioplasty or atherectomy.

In reference to the drawings, wherein like reference numerals denote like or corresponding parts throughout the drawing figures, and particularly to FIGS. 1–9, in the embodiments of a system and method in accordance with the invention, for example, a system 10 is provided for enabling an interventional procedure to be performed in a blood vessel 12 at an area of treatment 14. The system 10 is adapted to be atraumatic. It includes a guide wire 16 which enables the system 10 to be positioned distal to the area of treatment 14. The system 10 is placed within the carotid artery 18 or other blood vessel of the patient, and is guided into position by the guide wire 16. The guide wire 16 includes a distal end 20 thereof. The carotid artery 18 has the area of treatment 14 therein, which comprises the interventional procedure site, wherein atherosclerotic plaque 22 has built up against the inside wall 24, which decreases the diameter of the carotid artery 18. As a result, blood flow is diminished through this area.

The therapeutic interventional procedure comprises implanting an expandable interventional instrument at the interventional procedure site 14, to press the build-up of plaque 22 of the stenosis against the inside wall 24, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The expandable interventional instrument is expandable upon deployment thereof at the interventional procedure site 14.

The system 10 of the present invention enables the delivery of a filter device 26 to a location distal to the area of treatment 14, to enable deployment of the filter device 26 at the location distal to the area of treatment 14, and to enable the removal of the filter device 26 from the delivered and deployed position thereof. The filter device 26 filters the blood in the blood vessel 12, so as to pass blood therethrough and capture embolic material 28 which may be released in the blood vessel 12 during the interventional procedure. It is secured to the distal end 20 of the guide wire 16, so as to enable the filter device 26 to be placed within the carotid artery 18 or other blood vessel of the patient and guided into position distal to the area of treatment 14. The filter device 26 includes a proximal portion 30 and a distal portion 32.

Referring to FIGS. 1–9, in the embodiment of a system pursuant to the present invention, for example, the system 10 enables movement thereof through the patient's blood vessel 12 to a position distal to the area of treatment 14 for deployment of the filter device 26. The system 10 further enables expansion of the filter device 26 against the inside wall 24 of the blood vessel 12 and the sealing off of the inside wall 24, to enable the capture of embolic material 28 which may be released into the blood vessel 12 during the therapeutic interventional procedure.

The system 10 in accordance with the embodiment of the invention includes the guide wire 16, positionable within the blood vessel 12, and extendable to a position distal to the interventional procedure site 14. The system 10 also includes a fitting 34, secured to the distal end 20 of the guide wire 16, to which the proximal portion 30 of the filter device 26 is secured. The system 10 further includes the filter device 26, which is secured to the guide wire 16. The filter device 26 extends within a delivery sheath 36 for delivery to the interventional procedure site 14. The delivery sheath 36 includes a distal portion 38. The system 10 further includes an obturator 40, which includes a proximal end 42 and a distal end 44. The obturator 40 extends between the delivery sheath 36 and the distal end 20 of the guide wire 16, such that the distal end 44 of the obturator 40 extends along the distal end 20 of the guide wire 16, and the proximal end 42 of the obturator 40 is substantially abutted by the distal portion 38 of the delivery sheath 36 when the delivery sheath 36 is extended over the filter device 26. The obturator 40 provides a smooth transition between the delivery sheath 36 and the distal end 20 of the guide wire 16, so as to slide smoothly around tortuous anatomy in the blood vessel 12, and to inhibit digging into the inside wall 24 of the blood vessel 12 thereby.

The filter device 26 is deployed at the location in the patient's blood vessel 12 distal to the area of treatment 14, upon withdrawal of the delivery sheath 32. It captures embolic material 28 which may be released into the blood in the blood vessel 12 during the interventional procedure. The filter device 26 includes articulations, to enable the filter device 26 to navigate through tortuous anatomy, and to enable deployment thereof so as to seal against the inside wall 24 of the blood vessel 12.

In the embodiment in accordance with the invention, as illustrated in FIGS. 1–9, the filter device 26 includes a cage 46, which is secured to the guide wire 16, and filter material 48, for filtering embolic material 28, which is secured to the cage 46. The cage 46 includes a proximal portion 50 and a distal portion 52, and the filter material 48 includes a proximal end 54, a distal end 56, and a plurality of holes 58 for filtering embolic material 28.

The cage 46 further includes an articulating element 60, for enabling the cage 46 to articulate so as to move and flex during insertion thereof through the patient's vasculature 12. The articulating element 60 further enables the cage 46 to expand against and seal off the inside wall 24 of the blood vessel 12 upon deployment thereof, and to inhibit the cage 46 from contracting and pulling away from the blood vessel wall 24, to inhibit the formation of a gap through which embolic material 28 may otherwise flow. The cage 46 also includes a plurality of struts 62.

In a first version of the embodiment of a system pursuant to the present invention, as shown in FIGS. 1–7, the plurality of struts 62 comprise a plurality of proximal ribs 64, a plurality of distal ribs 66, and a ring 68, which extends intermediate the plurality of proximal ribs 64 and the plurality of distal ribs 66. The ring 68 comprises a preformed expandable shape, comprising an expandable maximum outer diameter portion, for expanding against the inside wall 24 of the blood vessel 12 upon expansion of the cage 46 for deployment thereof. Upon such expansion thereof, the ring 68, which forms the maximum outer diameter portion of the cage 46, also extends along and seals off the inside wall 24 of the blood vessel 12, to inhibit the formation of a gap between the cage 46 and the blood vessel inside wall 24 through which embolic material 28 may otherwise flow. The proximal end 54 of the filter material 48 is secured to the ring 68 which forms the maximum outer diameter portion of the cage 46. The ring 68, for example, includes a plurality of segments 70 and 72, and each adjacent pair of the plurality of segments 70 and 72 forms a contour which, for example, is a generally right-angle-bracket shape. The cross-sectional shape of the proximal ribs 64, the distal ribs 66, and the segments 70 and 72 of the ring 68, may for example be rectangular, square, or circular.

Each of the plurality of proximal ribs 64 includes a proximal portion 74 and a distal portion 76. Each of the plurality of distal ribs 66 includes a proximal portion 78 and a distal portion 80. Each of the plurality of segments 70 and 72 in the ring 68 includes a proximal portion 82 and a distal portion 84. The plurality of proximal ribs 64 and the plurality of distal ribs 66 may be comprised of stainless steel, and the plurality of segments 70 and 72 in the ring 68 may be comprised of Nitinol. The proximal portion 54 of the filter material 48 also includes a contour, which corresponds generally to the contour defined by the plurality of segments 70 and 72 of the ring 68.

In a first version of the embodiment of a system pursuant to the present invention, as shown in FIGS. 1–7, the articulating element 60 includes a proximal articulating element 86, located in the proximal portion 82 of each of the plurality of segments 70 and 72 in the ring 68, and a distal articulating element 88, located in the distal portion 84 of each of the plurality of segments 70 and 72 in the ring 68. Each pair of segments 70 and 72 which are adjacent to each other at the proximal ends 82 thereof comprise proximal adjacent segments 90. Each pair of segments 70 and 72 which are adjacent to each other at the distal ends 84 thereof comprise distal adjacent segments 92. Each pair of proximal adjacent segments 90 form a junction therebetween which comprises a proximal junction 94. The proximal junction 94 is in the form of a partial loop, which comprises a proximal partial loop 96. The distal portion 76 of each of the plurality of proximal ribs 64 is in the form of a loop which comprises a distal loop 98. Each distal loop 98 is engaged with each proximal partial loop 96, comprising proximal engaged loops and partial loops 100.

In the first version, each pair of distal adjacent segments 92 form a junction therebetween which comprises a distal junction 102. The distal junction 102 is in the form of a partial loop which comprises a distal partial loop 104. The proximal portion 78 of each of the plurality of distal ribs 66 is in the form of a loop, which comprises a proximal loop 106. The distal loop 98 and the proximal loop 106 may be formed by securing the overlapping portions thereof, for example by a band being wrapped therearound, or by being crimped, welded, or ultrasonically secured together. Each proximal loop 106 is engaged with each distal partial loop 104, comprising distal engaged loops and partial loops 108. The proximal articulating element 86 comprises the proximal engaged loops and partial loops 100. The distal articulating element 88 comprises the distal engaged loops and partial loops 108. Movement of each of the plurality of struts 62 so as to flex for articulation thereof is enabled by the proximal articulating element 86 and the distal articulating element 88, for enabling expansion of the filter device 26 in opposition to the inside wall 24 of the blood vessel 12, and inhibiting contraction thereof so as to inhibit gap formation through which embolic material 28 may otherwise flow.

Figure 5:
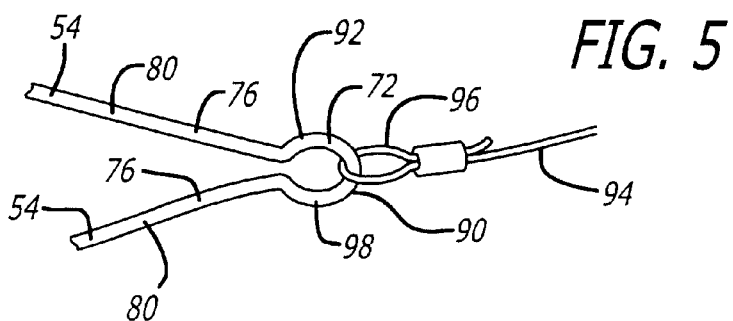
FIG. 5 is a fragmentary view of a portion of an articulating element in the filter device shown in FIG. 4.
Figure 7:
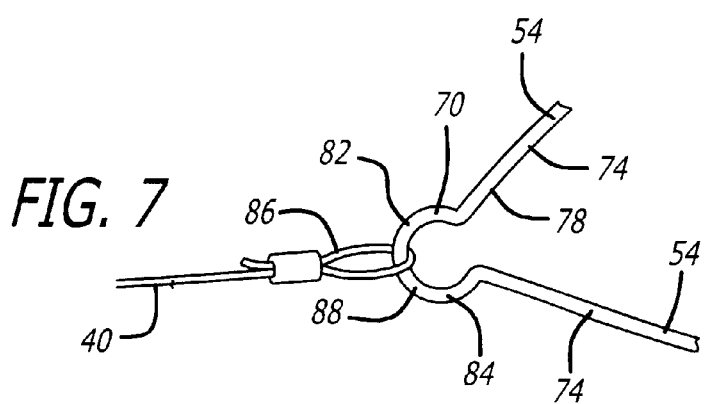
FIG. 7 is a fragmentary view of a portion of an articulating element in the filter device shown in FIG. 6.

In a first form of the first version of the embodiment in accordance with the invention, as seen in FIGS. 1–3, the articulating element 60 includes the proximal articulating element 86 and the distal articulating element 88. As depicted in FIGS. 4–5, in a second form of the first version of the embodiment of the present invention, the articulating element 60 comprises the distal articulating element 88. The articulating element 60, in a third form of the first version of the embodiment pursuant to the invention, as illustrated in FIGS. 6–7, comprises the proximal articulating element 86.

As shown in FIGS. 8–9, in a second version of the embodiment in accordance with the invention, in the form thereof seen in FIG. 8, the articulating element 60 comprises a generally u-shaped portion 110 of each of the plurality of proximal ribs 64. The generally u-shaped portion 110 is spaced from the proximal portion 74 and the distal portion 76 of each of the plurality of proximal ribs 64. It enables each of the plurality of struts 62 to move and flex for articulating thereof, so as to inhibit the cage 34 from contracting away from the blood vessel wall 24, and to enable the filter device 26 to navigate through tortuous vasculature 12. In another form of the second version of the embodiment of the invention depicted in FIG. 9, the articulating element 60 comprises a generally w-shaped portion 112 of each of the plurality of proximal ribs 64. The generally w-shaped portion 112 is spaced from the proximal portion 74 and the distal portion 76 of each of the plurality of proximal ribs 64. Each of the plurality of struts 62 articulates to inhibit the cage 46 from pulling away from the blood vessel wall 24, and to enable the filter device 26 to navigate through tortuous vasculature 12.

Referring to FIGS. 1–9, in a method for the use of the embodiment of a system in accordance with the present the invention, for example, the system 10 enables movement of the system 10 through the patient's blood vessel 12 to the location for deployment of the filter device 26, and seals off the inside wall 24 of the blood vessel 12 to enable the capture of embolic material 28. The filter device 26 is assembled and is secured to the fitting 34 at the distal end 20 of the guide wire 16. The delivery sheath 36 is extended over the guide wire 16 so as to enclose the filter device 26 therein, such that the distal portion 38 of the delivery sheath 36 substantially abuts the proximal end 42 of the obturator 40.

The system 10 is positioned in the patient's vasculature 12 utilizing any one of a number of different methods. In one preferred method of positioning the system 10, the delivery sheath 36, with the filter device 26 therein, is inserted into and extended through the patient's vasculature 12, to cross the stenosis in the blood vessel 12, so as to extend to a position distal to the interventional procedure site 14. The filter device 26 articulates as it moves through the patient's vasculature 12. The delivery sheath 36 is then withdrawn, enabling the filter device 26 to deploy so as to capture embolic material which may be released in the blood vessel 12 during the interventional procedure.

After the delivery sheath 36 is withdrawn, the filter device 26 is released from being enclosed in the delivery sheath 36. The filter device 26 then expands, bearing against the inside wall 24 of the blood vessel 12. The filter device 26 flexes and moves so as to articulate as it expands, enabling it to press against the inside wall 24 of the blood vessel 12, to seal off the inside wall 24 of the blood vessel 12, and to inhibit the formation of a gap between the filter device 30 and the blood vessel wall 24, through which embolic material 28 may otherwise flow. The filter material 48 expands with the flow of blood in the blood vessel 12 therethrough, to capture embolic material 28 which may be released during the interventional procedure.

In the first version of the embodiment of the present invention, as seen in FIGS. 1–7, in the first form thereof as seen in FIGS. 1–3, the filter device 26 moves and flexes so as to articulate through the patient's anatomy 12, and into deployed position thereof at the location distal to the area of treatment 14, responsive to the proximal articulating element 86 and the distal articulating element 88. As shown in FIGS. 4–5, in the second form of the first version of the embodiment thereof, the articulation of the filter device 26 is provided by flexing and movement of the distal articulating element 88, during insertion thereof through the patient's vasculature 12, and during deployment thereof at the area of treatment 14. In the third form of the first version of the embodiment pursuant to the present invention, as depicted in FIGS. 6–7, the flexing and movement for articulation of the filter device 26 through the patient's anatomy 12 and upon deployment at the area of treatment 14 is provided by the proximal articulating element 86.

As illustrated in FIGS. 8–9, in the second version of the embodiment in accordance with the invention, the filter device 26 articulates as it moves through the patient's vasculature 12. The articulation results from flexing and movement of the generally u-shaped portion 110 of each of the plurality of proximal ribs 64, in the form in FIG. 8, and from such articulating movement of the generally w-shaped portion 112 of the plurality of proximal ribs 64, in the form in FIG. 9.

In accordance with the present invention, the particular embodiments set forth above of the system 10 for filtering embolic material are capable of being positioned in a blood vessel. However, other forms of the system 10 may be utilized with the present invention without departing from the spirit and scope of the invention. For example, the system 10 may be comprised of other forms of material. Additionally, while the system 10 is shown as in various shapes in the embodiments herein, it can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the above, it is apparent that the system and method of the present invention enhances substantially the effectiveness of performing interventional procedures by providing a filter device for filtering embolic material, which articulates by flexing and moving during insertion thereof through the patient's anatomy. The system and method further enable the filter device to articulate upon deployment thereof at the location distal to the interventional procedure site, to expand against the inner wall of a blood vessel so as to seal off the inner surface thereof, to inhibit gap formation and the passing of embolic material therethrough.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed is:

1. A system for enabling the capture of embolic material which may be released into a blood vessel during a therapeutic interventional procedure, comprising:

a guide wire, including a distal end, adapted to be positioned within the blood vessel and to extend to a position distal to the interventional procedure site; and a filter device, adapted to be positioned and deployed at a location in the patient's vasculature distal to the interventional procedure site, and to capture embolic material which may be released into the blood in the blood vessel during the interventional procedure, including an articulating element, for enabling the filter device to articulate so as to move and flex during insertion through the blood vessel, and to expand against the inner surface of the wall of the blood vessel, and seal off the inner surface of the blood vessel wall, upon expansion of the filter device for deployment thereof, so as to inhibit the formation of a gap between the filter device and the blood vessel wall through which embolic material may otherwise flow.

2. The system of claim 1, wherein the filter device includes a cage, secured to the distal end of the guide wire, and filter material, for filtering embolic material, secured to the cage.

3. The system of claim 1, wherein the cage includes a plurality of struts, each of which includes a plurality of proximal ribs, a plurality of distal ribs, and a ring which extends intermediate the plurality of proximal ribs and the plurality of distal ribs, which forms a proximal junction between the plurality of proximal ribs, and a distal junction between the plurality of distal ribs, and wherein the articulating element includes a proximal articulating element, located at the proximal junction, and a distal articulating element, located at the distal junction.

4. The system of claim 3, further comprising a fitting, secured to the distal end of the guide wire, and wherein the plurality of proximal ribs are connected to the fitting.

5. The system of claim 3, wherein the ring includes a plurality of segments, each of which includes a proximal portion and a distal portion, and wherein each pair of segments which are adjacent to each other at the proximal ends thereof comprise proximal adjacent segments, and each pair of segments which are adjacent to each other at the distal ends thereof comprise distal adjacent segments.

6. The system of claim 5, wherein each of the plurality of proximal ribs includes a distal portion, each of the plurality of distal ribs includes a proximal portion, each pair of proximal adjacent segments form a junction therebetween which comprises a proximal junction, the proximal junction is in the form of a partial loop which comprises a proximal partial loop, the distal portion of each of the plurality of proximal ribs is in the form of a loop which comprises a distal loop, and each distal loop is engaged with each proximal partial loop comprising proximal engaged loops and partial loops, each pair of distal adjacent segments form a junction therebetween which comprises a distal junction, the distal junction is in the form of a partial loop which comprises a distal partial loop, the proximal end of each of the plurality of distal ribs is in the form of a loop which comprises a proximal loop, and each proximal loop is engaged with each distal partial loop, comprising distal engaged loops and partial loops, and wherein the proximal articulating element comprises the proximal engaged loops and partial loops, and the distal articulating element comprises the distal engaged loops and partial loops.

7. The system of claim 5, wherein the plurality of segments of the ring define a contour thereof.

8. The system of claim 7, wherein the filter device includes filter material, secured to the plurality of segments of the ring, the filter material includes a proximal portion and a distal portion, and the proximal portion of the filter material includes a contour which corresponds generally to the contour defined by the plurality of segments of the ring.

9. The system of claim 7, wherein the contour defined by the plurality of segments of the ring is generally right-angle-bracket shaped.

10. The system of claim 1, wherein the cage includes a plurality of struts, each of which includes a plurality of proximal ribs, a plurality of distal ribs, and a ring which extends intermediate the plurality of proximal ribs and the plurality of distal ribs, which forms a distal junction between the plurality of distal ribs, and wherein the articulating element comprises a distal articulating element, located at the distal junction.

11. The system of claim 10, wherein the ring includes a plurality of segments, each of which includes a proximal portion and a distal portion, and wherein each pair of segments which are adjacent to each other at the distal ends thereof comprise distal adjacent segments.

12. The system of claim 11, wherein each of the plurality of proximal ribs includes a distal portion, each of the plurality of distal ribs includes a proximal portion, each pair of distal adjacent segments form a junction therebetween which comprises a distal junction, the distal junction is in the form of a partial loop which comprises a distal partial loop, the proximal end of each of the plurality of distal ribs is in the form of a loop, which comprises a proximal loop, and each proximal loop is engaged with each distal partial loop comprising distal engaged loops and partial loops, and wherein the distal articulating element comprises the distal engaged loops and partial loops.

13. The system of claim 11, wherein the plurality of segments of the ring define a contour thereof.

14. The system of claim 13, wherein the filter device includes filter material, secured to the plurality of segments of the ring, the filter material includes a proximal portion and a distal portion, and the proximal portion of the filter material includes a contour which corresponds generally to the contour defined by the plurality of segments of the ring.

15. The system of claim 13, wherein the contour defined by the plurality of segments of the ring is generally right-angle-bracket shaped.

16. The system of claim 1, wherein the cage includes a plurality of struts, each of which includes a plurality of proximal ribs, a plurality of distal ribs, and a ring which extends intermediate the plurality of proximal ribs and the plurality of distal ribs, which forms a proximal junction between the plurality of proximal ribs, and wherein the articulating element comprises a proximal articulating element, located at the proximal junction.

17. The system of claim 16, wherein the ring includes a plurality of segments, each of which includes a proximal portion and a distal portion, and wherein each pair of segments which are adjacent to each other at the proximal ends thereof comprise proximal adjacent segments.

18. The system of claim 17, wherein each of the plurality of proximal ribs includes a distal portion, each of the plurality of distal ribs includes a proximal portion, each pair of proximal adjacent segments form a junction therebetween which comprises a proximal junction, the proximal junction is in the form of a partial loop which comprises a proximal partial loop, the distal portion of each of the plurality of proximal ribs is in the form of a loop, which comprises a distal loop, and each distal loop is engaged with each proximal partial loop comprising proximal engaged loops and partial loops, and wherein the proximal articulating element comprises the proximal engaged loops and partial loops.

19. The system of claim 17, wherein the plurality of segments of the ring define a contour thereof.

20. The system of claim 19, wherein the filter device includes filter material, secured to the plurality of segments of the ring, the filter material includes a proximal portion and a distal portion, and the proximal portion of the filter material includes a contour which corresponds generally to the contour defined by the plurality of segments of the ring.

21. The system of claim 19, wherein the contour defined by the plurality of segments of the ring is generally right-angle-bracket shaped.

22. A system for enabling the capture of embolic material which may be released into a blood vessel during a therapeutic interventional procedure, comprising:

a guide wire, including a distal end, adapted to be positioned within the blood vessel and to extend to a position distal to the interventional procedure site; and a filter device, adapted to be positioned and deployed at a location in the patient's vasculature distal to the interventional procedure site, and to capture embolic material which may be released into the blood in the blood vessel during the interventional procedure, including an articulating element, for enabling the filter device to be inserted through the blood vessel so as to move and flex to articulate therein, for enabling the filter device to navigate through confined spaces therein.

23. The system of claim 22, wherein the filter device includes a cage, secured to the distal end of the guide wire, and filter material, for filtering embolic material, secured to the cage.

24. The system of claim 23, wherein the cage includes a plurality of struts, each of which includes a plurality of proximal ribs, and wherein each of the plurality of proximal ribs includes the articulating element therein.

25. The system of claim 24, wherein each of the plurality of proximal ribs includes a proximal end and a distal end, and the articulating element comprises a generally u-shaped portion of the proximal portion of each of the plurality of proximal ribs, spaced from the proximal end and the distal end thereof.

26. The system of claim 24, wherein each of the plurality of proximal ribs includes a proximal end and a distal end, and the articulating element comprises a generally w-shaped portion of the proximal portion of each of the plurality of proximal ribs, spaced from the proximal end and the distal end thereof.

27. A method of enabling the capture of embolic material which may be released into a blood vessel during a therapeutic interventional procedure, in a system which comprises a guide wire, including a distal end, adapted to be positioned within the blood vessel and to extend to a position distal to the interventional procedure site, and a filter device, adapted to be positioned and deployed at a location in the patient's vasculature distal to the interventional procedure site, and to capture embolic material which may be released into the blood in the blood vessel during the interventional procedure, including an articulating element, for enabling the filter device to articulate so as to move and flex during insertion through the blood vessel, and to expand against the inner surface of the wall of the blood vessel, and seal off the inner surface of the blood vessel wall, upon expansion of the filter device for deployment thereof, so as to inhibit the formation of a gap between the filter device and the blood vessel wall through which embolic material may otherwise flow, wherein the method comprises:

inserting the guide wire, and the filter device secured to the distal end thereof, through the blood vessel, to the position distal to the interventional procedure site; and deploying the filter device at the position distal to the interventional procedure site, wherein the articulating element articulates, enabling the filter device to expand against the inner surface of the wall of the blood vessel, and seal off the inner surface of the blood vessel wall, so as to inhibit the formation of a gap between the filter device and the blood vessel wall through which embolic material may otherwise flow.

28. A method of enabling the capture of embolic material which may be released into a blood vessel during a therapeutic interventional procedure, in a system which comprises, a guide wire, including a distal end, adapted to be positioned within the blood vessel and to extend to a position distal to the interventional procedure site, and a filter device, adapted to be positioned and deployed at a location in the patient's vasculature distal to the interventional procedure site, and to capture embolic material which may be released into the blood in the blood vessel during the interventional procedure, including an articulating element, for enabling the filter device to be inserted through the blood vessel so as to move and flex to articulate therein, for enabling the filter device to navigate through confined spaces therein, wherein the method comprises:

inserting the guide wire, and the filter device secured thereto and unexpanded within a delivery sheath, through the blood vessel, to the position distal to the interventional procedure site, wherein the articulating element articulates, enabling the filter device to navigate through confined spaces in the blood vessel; and deploying the filter device at the position distal to the interventional procedure site.

* * * * *